(12) United States Patent
Imai

(10) Patent No.: US 6,597,004 B2
(45) Date of Patent: Jul. 22, 2003

(54) POWDERED FAR-INFRARED RADIATOR AND METHOD OF MAKING THE SAME

(76) Inventor: Koichi Imai, 433, Momoyama-cho 2-chome, Kasugai, Aichi (JP)

( * ) Notice: Subject to any disclaimer, the term of this patent is extended or adjusted under 35 U.S.C. 154(b) by 0 days.

(21) Appl. No.: 10/191,500

(22) Filed: Jul. 10, 2002

(65) Prior Publication Data

US 2003/0042435 A1 Mar. 6, 2003

(30) Foreign Application Priority Data

Aug. 23, 2001 (JP) ......................................... 2001-252830

(51) Int. Cl.$^7$ ............................. G01J 1/00; G21G 4/00; F24C 7/00
(52) U.S. Cl. ............................. 250/493.1; 250/495.1; 250/493.1; 392/407; 252/500; 252/587; 252/508
(58) Field of Search ............................. 250/493.1, 504 R, 250/495.1; 392/407; 252/500, 587, 508

(56) References Cited

U.S. PATENT DOCUMENTS

| | | | | |
|---|---|---|---|---|
| 4,965,434 A | * | 10/1990 | Nomura et al. | 252/587 |
| 5,419,855 A | * | 5/1995 | Kikuta | 252/587 |
| 6,004,588 A | * | 12/1999 | Torii et al. | 424/682 |
| 6,012,304 A | * | 1/2000 | Loxley et al. | 65/111 |
| 6,402,991 B1 | * | 6/2002 | Itakura et al. | 252/500 |

FOREIGN PATENT DOCUMENTS

| | | | | |
|---|---|---|---|---|
| CN | 1085577 A | * | 4/1994 | C08K/3/38 |
| JP | 60134126 | * | 12/1983 | F24C/15/24 |
| JP | 63092720 | * | 4/1988 | D01F/8/04 |
| JP | 01308484 | * | 6/1988 | C09K/9/00 |
| JP | 03017004 | * | 6/1989 | A61K/7/00 |
| JP | 02085210 | * | 3/1990 | A61K/9/70 |
| JP | 02154009 | * | 6/1990 | D01F/8/04 |
| JP | 02180835 | * | 7/1990 | A61K/47/02 |
| JP | 03146304 | * | 6/1991 | B27K/3/52 |
| JP | 03213653 | * | 9/1991 | F02M/27/06 |
| JP | 05117902 | * | 10/1991 | A41B/11/00 |
| JP | 05230692 | * | 2/1992 | C25D/11/04 |
| JP | A 10-5265 | | 1/1998 | |
| KR | 9508584 | * | 8/1995 | C04B/14/10 |

* cited by examiner

*Primary Examiner*—John R. Lee
*Assistant Examiner*—James P. Hughes
(74) *Attorney, Agent, or Firm*—Oliff & Berridge, PLC

(57) ABSTRACT

A powdered far-infrared radiator includes a quartz schist pulverized into a powder having a grain diameter not exceeding 6 μm and heat-treating the powder at or above 200° C. The quartz schist radiates far-infrared rays at an ordinary temperature.

8 Claims, 4 Drawing Sheets

POWDERED FAR-INFRARED RADIATOR AND METHOD OF MAKING THE SAME

BACKGROUND OF THE INVENTION

1. Field of the Invention

This invention relates to a powdered far-infrared radiator radiating far-infrared rays at an ordinary temperature and a method of making the powdered far-infrared radiator.

2. Description of the Related Art

Far-infrared trays can be used as a high efficient thermal energy and have a bactericidal action, an antioxidant action, etc. all of which have been tried to be used in various fields. The inventor found that a type of quartz schist radiated far-infrared rays even at an ordinary temperature, namely, at or below 20° C. In order that the quartz schist radiating far-infrared rays at the ordinary temperature may be provided as a high practical and valuable product, the inventor then invented a novel far-infrared radiator and a method of making the far-infrared radiator. In this method, the quartz schist is pulverized into powder having a grain diameter ranging 75 $\mu$m to 35 $\mu$m. The powder is then mixed with powdered stainless steel, and the mixture is shaped into a predetermined shape and sintered. A patent application was filed for the invention in Japan and assigned with patent application number of 8-164292.

The far-infrared radiator of the above-described type serves as a hot compress pack facilitating blood circulation when applied to parts of a human body. However, the foregoing far-infrared radiator is generally formed into a hard solid state such as the shape of a tablet or plate. When applied to a human body, a tablet-shaped radiator is sewn in a pocket formed on a band-shaped piece of cloth or the like. Thus, the radiator is limited in its mode of use. Accordingly, a range of use of the far-infrared radiator is desired to be increased.

SUMMARY OF THE INVENTION

Therefore, an object of the present invention is to provide a powdered far-infrared radiator which radiates far-infrared rays at an ordinary temperature and which can be used in various forms, thereby increasing a range of use thereof, and a method of making the powdered far-infrared radiator.

The inventor found that quartz schist mined at or near Mount Deki located at a northeastern part of Aichi prefecture in Japan (Shitara-cho, Kitashitara-gun) radiated far-infrared rays even at an ordinary temperature, namely, at or below 20° C. The quartz schist contains $SiO_2$ as a main component. The quartz schist in the foregoing district is guessed to have obtained the property of radiating far-infrared rays during formation for geographic or stratigraphic reasons, which property differs from those of other types of quartz schist. The geographic or stratigraphic reasons include one that the quartz schist layer lies near a tectonic line.

The aforementioned quartz schist having the characteristic of radiating far-infrared rays at an ordinary temperature was pulverized into a powder having a grain diameter not exceeding 6 $\mu$m with the bulk specific gravity being reduced. The inventor ascertained that the grains were uniformly dispersed (suspended) without precipitating even when the powder was mixed with a liquid, cream, gel such as adhesive agent, thereby having made the present invention. The inventor further found that when the powder was heat-treated at or above 200° C., a radiating efficiency of the powdered far-infrared radiator was increased as compared with a case where the powder was not heat-treated.

In one aspect, the present invention provides a powdered far-infrared radiator comprising a quartz schist pulverized into a powder having a grain diameter not exceeding 6 $\mu$m and heat-treating the powder at or above 200° C., the quartz schist radiating far-infrared rays at an ordinary temperature.

In another aspect, the invention provides a method of making a powdered far-infrared radiator comprising pulverizing a quartz schist into a powder having a grain diameter not exceeding 6 $\mu$m by means of wet grinding, the quartz schist radiating far-infrared rays at an ordinary temperature and heat-treating the pulverized powder at or above 200° C.

The above-described quartz schist is pulverized into the powder having the grain diameter not exceeding 6 $\mu$m. Consequently, the powdered far-infrared radiator can uniformly be dispersed even when mixed with a liquid or cream. Accordingly, the powdered far-infrared radiator can take various forms when actually used, so that a range of use thereof can be increased. Furthermore, a surface area of the radiator can be increased to a large extent since the radiator is powdered. The radiating efficiency of the radiator can further be improved by the heat treatment. Additionally, the permeability of the radiator from human skin can be improved when the radiator is caused to act upon a human body. Consequently, an efficacy of the radiator can be improved.

In making the powdered far-infrared radiator, a raw ore of the quartz schist is pulverized by means of wet grinding using a ball mill with ceramic. Thereafter, only the powder having a grain diameter not exceeding 6 $\mu$m is extracted using a vibratory screen, for example. In the heat treatment, the obtained powder is heated at or above 200° C. or more specifically, at or above 300° C., whereupon a heat-treatment time can be shortened.

The powdered far-infrared radiator of the present invention is fine powdered as described above and has a characteristic of radiating far-infrared rays at the ordinary temperature. Accordingly, the radiator can be used for purposes including application to a human body for facilitation of the blood circulation due to the characteristic thereof, namely, heating action (far-reachingness). Furthermore, a bactericidal action and an antibacterial action (antioxidant action) of the far-infrared rays can be utilized. More specifically, the powdered far-infrared radiator of the invention can be used in the following forms and purposes. Firstly, the powdered far-infrared radiator may be included in a cream or liquid so as to be used as a cosmetic or medicine both applied to a skin. Consequently, since the radiator is easily applied to human skin, its characteristic of radiating far-infrared rays can be utilized as the cosmetic or medicine both applied to the skin.

More specifically, when mixed with a facial cream, hand cream, beauty wash or toilet lotion, milky lotion, etc., the radiator can improve the cosmetic effects of skin cosmetics including prevention of skin irritation, spots, freckles, etc. Furthermore, when mixed with a medicated cream, a cream (ointment) used for first aid or the like in sports, etc., the radiator can improve skin troubles such as atopic dermatitis, ease the stiffness in the shoulders, pain in the knee, lumbago, bruise, sprain, muscular pain, etc. The radiator can further improve effects of plasters for sterilization of external wound, inflammation, etc., disinfection, pain-killing, antiphlogistic, etc. When mixed with the cream or the like, the powdered far-infrared radiator preferably ranges 5 to 20 weight percentage (wt. %). The radiator has a conspicuous effect on the improvement in the atopic dermatitis particularly when an amount thereof is increased to about 30 wt %.

The powdered far-infrared radiator may be held directly on a cloth-like holder or indirectly on a member bonded to the holder, whereby the radiator serves for care or first aid as a taping member as used in sports, poultice, or sticking or adhesive plaster. Thus, the powdered far-infrared radiator can easily be held on the cloth-like holder such as cloth, paper, plastic film, etc. When the cloth-like holder is applied to or wound on a human body, the characteristic of radiating far-infrared rays can be utilized for care or first aid.

When held on the cloth-like holder, the powdered far-infrared radiator may be mixed with an adhesive agent to be applied to the cloth-like holder. Regarding cloth and paper, the radiator may be caused to permeate fiber or thread which is woven into the cloth, thereby to be held. The powdered far-infrared radiator used preferably ranges 0.5 to 3 g per centare. Furthermore, when mixed with an adhesive agent, the powdered far-infrared radiator used preferably ranges 3 to 5 wt. %.

More specifically, the powdered far-infrared radiator can be used as a taping member as used in sports (called "kinesiotape") or the like by holding the radiator on a tape or bandage, whereupon improvements in the pain soothing and protection of an affected part can be achieved. Furthermore, when a plaster mixed with the powdered far-infrared radiator is applied to the cloth-like holder, the plaster can be used as a poultice (antiphlogistic agent). When the radiator is held on a first aid commodity such as plaster, gauze or bandage, a wound can be cured faster. The radiator may be applied to a first-aid plaster which has a centrally located disinfecting gauze. In this case, the radiator may be held on the disinfecting gauze or on a tape portion. Additionally, the radiator held on the cloth-like holder may be used as a packing member for beauty. Consequently, a good effect can be achieved for skin. When the radiator held on the cloth-like holder is attached to eyes of a sufferer, the sufferer can be relieved from asthenopia.

Furthermore, the inventor confirmed that the powdered far-infrared radiator was able to improve the functions of internal organs of a human body thereby to provide a desirable physical condition and promote one's health when orally taken into the human body. Accordingly, the powdered far-infrared radiator is preferably mixed with a beverage or food so as to be used for promotion of one's health. In this case, one's health can be promoted when one just drinks a solution of the radiator in water. When the radiator is used for eating and drinking purposes, the grain diameter thereof is preferably reduced to be at or below 0.8 $\mu$m.

Additionally, the powdered far-infrared radiator can be used as a product facilitating blood circulation in a human body when applied to personal ornaments including clothing and bedding such as "futon" or thick bedquilt, bed sheets and mattress. In this case, the powdered far-infrared radiator may be mixed with cotton wool of the "futon" as well as held on cloth. The radiator can further serve as an insole for shoes by making use of a bactericidal action and an antibacterial action thereof. The radiator can still further serve as a material for packaging perishable foods and be mixed with a paint, whereupon a range of use of the radiator can be increased.

BRIEF DESCRIPTION OF THE DRAWINGS

Other objects, features and advantages of the invention will become clear upon reviewing the following description of embodiment, made with reference to the accompanying drawings, in which.

DETAILED DESCRIPTION OF THE INVENTION

One embodiment of the present invention will be described with reference to the accompanying drawings. A powdered far-infrared radiator A of the embodiment is made by grinding a quartz schist B into powder having a grain diameter not exceeding 6 $\mu$m or more specifically, not exceeding 1.6 $\mu$m in the embodiment and further by heating the powder at 200° C. or above or more specifically, at a temperature ranging from 300° C. to 400° C. The quartz schist B has a characteristic of radiating far-infrared rays at an ordinary temperature.

Figure 1:
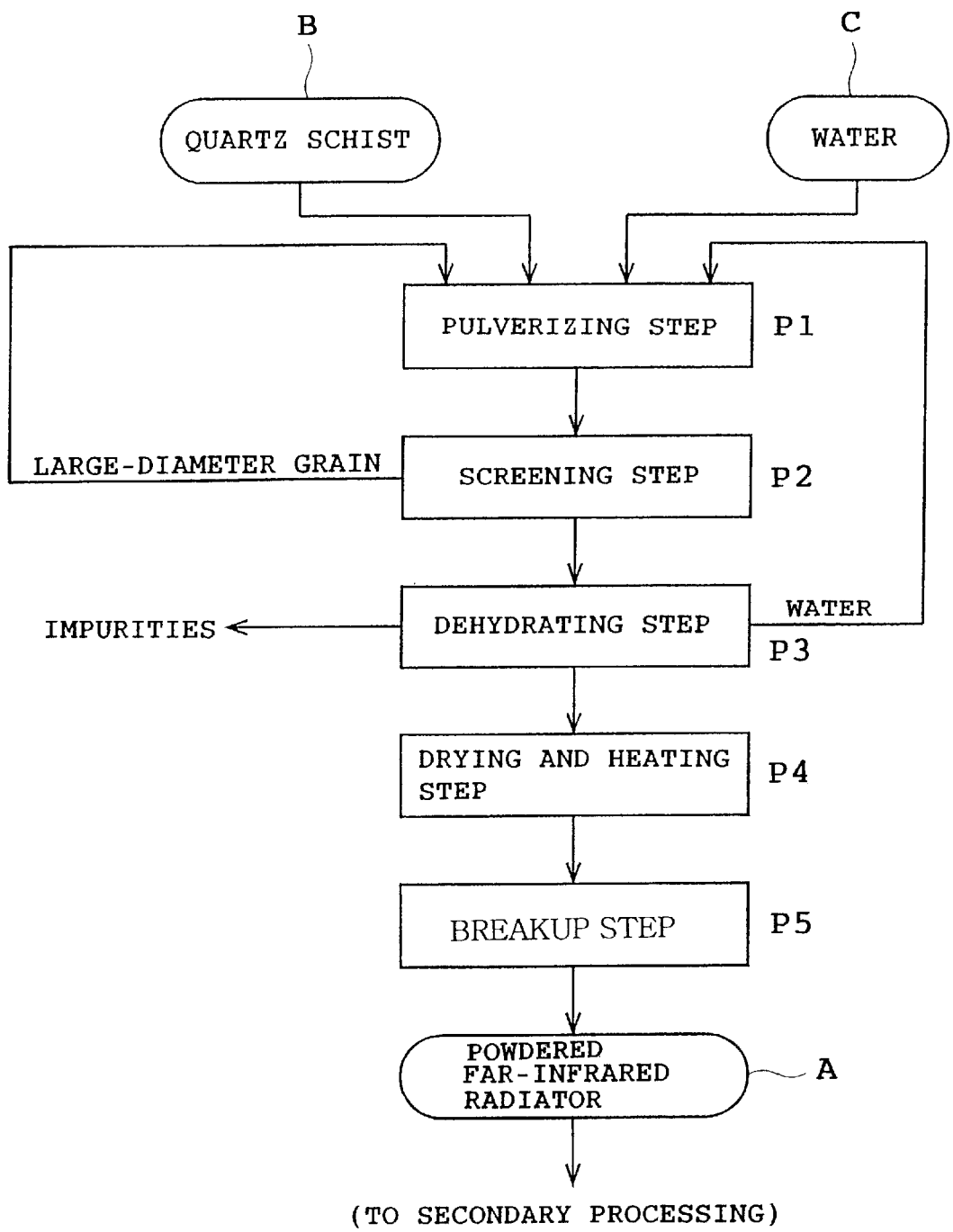
FIG. 1 schematically illustrates steps for making the powdered far-infrared radiator of one embodiment in accordance with the present invention.

FIG. 1 schematically illustrates steps for making the foregoing powdered far-infrared radiator A. The steps will now be described. The quartz schist B as the material for the powdered far-infrared radiator is obtained in or near Mount Deki located on the northeastern part (Shitara-cho, Kitashitara-gun) of Aichi prefecture, Japan, for example. The quartz schist B radiates a sufficient amount of far-infrared rays even at a low temperature of 20° C. or below (ordinary temperature). A currently general analysis method reveals that the quartz schist B comprises 80 to 90 wt. % $SiO_2$ as a main component, 8 to 9 wt. % $Al_2O_3$, 0.7 to 0.8 wt. % $Fe_2O_3$, and a small amount of each of $TiO_2$, CaO, MgO, $K_2O$ and $Na_2O$. TABLE 1 shows the result of elemental analysis regarding a sample of the quartz schist B.

TABLE 1

| Na | Mg | Al | Si | P | S | K | Ti | Mn | Fe | O | Cr |
|---|---|---|---|---|---|---|---|---|---|---|---|
| 1.6 | 0.25 | 7.2 | 62.5 | 0.030 | 0.22 | 2.2 | 0.16 | 0.019 | 0.68 | 25.7 | ≦0.10 (by wt. %) |

| Be | F | Cl | V | Co | Ni | As | Zr | Mo | Ag | Te | Hf | W | Pb |
|---|---|---|---|---|---|---|---|---|---|---|---|---|---|
| 5 | 8 | ≦85 | ≦15 | 4 | 10 | 3 | 28 | 5 | 20 | 2 | 7 | 3 | 13 (by ppm) |

In making the powdered far-infrared radiator A, a pulverizing or grinding step P1 is carried out so that the aforementioned quartz schist B is pulverized or ground by means of wet grinding. A general purpose wet grinder wet grinding machine such as a ball mill employing alumina balls is used in the grinding step P1. The quartz schist B is accommodated in the grinding machine together with water C. The grinding machine is driven for example, for 50 to 70 hours so that the quartz schist B is ground into fine powder.

A screening step P2 is subsequently carried out so that the ground quartz schist having a grain diameter which is at or below a predetermined value is taken out. A vibratory screen with a mesh of 1.6 μm is employed in the screening step P2. Consequently, only the finely powdered grain having the grain diameter which is not exceeding 1.6 μm is extracted. The remainder having the grain diameter equal to or exceeding 1.6 μm is returned to the grinding step P1 to be re-ground in a subsequent making.

The finely powdered grain extracted at the screening step P2 contains water C (suspended in water C). Accordingly, a predetermined dehydrating operation is executed at a subsequent dehydration step P3. A suspension of fine powder of the quartz schist B is put into a precipitation tank to be left, for example, for 10 to 24 hours. Supernatant (water C) is eliminated while the fine powder of quartz schist B is precipitated. The precipitate is then dehydrated by means of pressing, whereupon about 70% water is eliminated from the precipitate. Consequently, cake-like fine powder of quartz schist B is obtained. The eliminated water is recycled in a subsequent making. Impurities such as mica are also eliminated as well as the supernatant.

Figure 2:
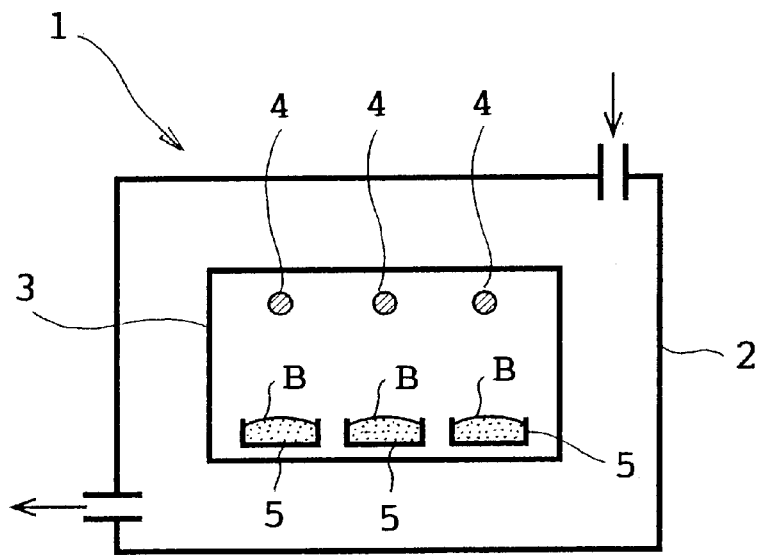
FIG. 2 schematically illustrates a drying chamber.

A drying and heating step P4 is then carried out so that the cake-like fine powder of quartz schist B is dried and heat-treated. FIG. 2 schematically illustrates a drying chamber 1 in which the drying and heating step P4 is executed. The drying chamber 1 has a double chamber structure, that is, includes an outer chamber 2 and an inner chamber 3 defined in the outer chamber. Drying hot air is supplied into the outer chamber 2 along an inner wall. A heater 4 such as an infrared heater is provided in the inner chamber 3. A number of, for example, stainless trays 5 each of which is filled with an appropriate amount of cake-like fine powder of the quartz schist B are set in the inner chamber 3.

In the drying and heating step P4, hot air whose temperature ranges 60° C. to 90° C. is circulated through the outer chamber 2 so that the cake-like fine powder of the quartz schist B is dried. The drying is carried out for 50 to 70 hours, for example, so that water is eliminated from the cake-like fine powder of the quartz schist B. At the end of the drying, the heater 4 is energized for heat treatment of the cake-like fine powder of the quartz schist B. As a result, a temperature in the inner chamber 3 is increased to 300° C. to 400° C. The heat treatment of the cake-like fine powder of the quartz schist B is executed in this atmosphere, for example, for 30 to 40 minutes.

The fine powder of the quartz schist B is solid in the shape of a cake when the drying and heating step P4 is finished. Accordingly, the obtained fine powder of the quartz schist B is broken up into pieces using a dry grinding machine such as a pin mill at a breakup step P5, whereby the powdered far-infrared radiator A is obtained. The obtained radiator A is supplied as product or secondly treated.

The above-described powdered far-infrared radiator A is manufactured by grinding the quartz schist having the characteristic of radiating far-infrared rays at an ordinary temperature into a powder having a grain diameter not exceeding 6 μm or more specifically, not exceeding 1.6 μm. Accordingly, since the specific gravity of the radiator is reduced, the grains can uniformly be dispersed (suspended) without precipitating even when the powder was mixed with a liquid, cream, and gel such as adhesive agent. Consequently, the radiator A can be used in various forms, making use of a heating action (far-reachingness), bactericidal action and antibacterial action of the far-infrared rays, whereupon a range of use of the radiator A can be increased.

Furthermore, a surface area of the radiator A can be increased to a large extent since the radiator is powdered. Consequently, the far-infrared ray radiating efficiency of the radiator can further be improved exceedingly. Additionally, since the radiator A is heat treated at the temperature exceeding 200° C., more specifically, ranging 300° C. to 400° C., the radiating efficiency of the radiator can further be improved. When the radiator A is heat treated at the temperature exceeding 200° C., the far-infrared ray radiating efficiency of the radiator can be improved by about 30% as compared with the case where no heat-treatment is carried out. Moreover, the permeability of the radiator from human skin can be improved when the radiator is caused to act upon a human body. Consequently, an efficacy of the radiator can be improved as follows.

Figure 3:
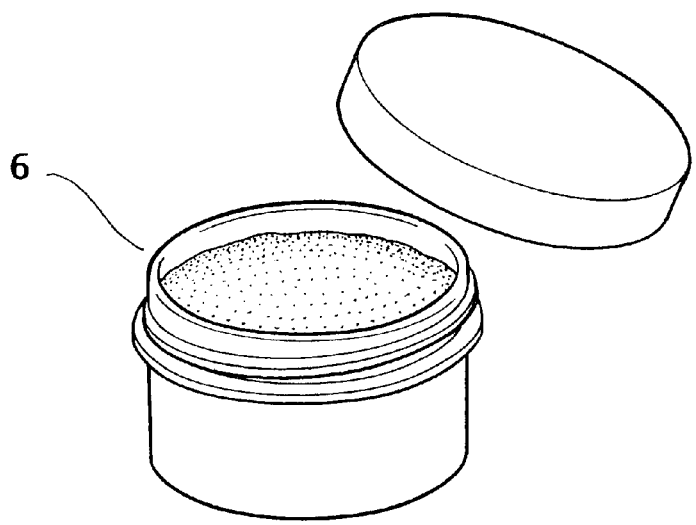
FIG. 3 illustrates a cream to which the powdered far-infrared radiator is applied.

Several examples of use of the powdered far-infrared radiator A will now be described. Firstly, as described above, the powdered far-infrared radiator A can be dispersed uniformly when mixed with a cream or liquid. Accordingly, the radiator A can be used as a cosmetic or medicine both applied to a skin. More specifically, as shown in FIG. 3, the radiator A can be mixed with a cream 6 such as a facial cream or hand cream at the rate of 5 to 20 wt. %. Consequently, an effect good for the skin, for example, facilitation of blood circulation can be achieved when the cream 6 is applied to a face, hands, etc. Accordingly, the radiator A can improve the cosmetic effects of skin-applied cosmetics including prevention of skin irritation, spots, freckles, etc. Furthermore, the powdered far-infrared radiator A can be mixed with lotion or milky lotion.

Furthermore, when mixed with medicated cream, sports cream (ointment), etc., the radiator A can improve skin troubles such as atopic dermatitis, ease the stiffness in the shoulders, pain in the knee, lumbago, bruise, sprain, muscular pain, etc. The radiator can further improve effects of plasters for sterilization of external wound, inflammation, etc., disinfection, pain-killing, antiphlogistic, etc. The radiator A is further effective against asthma and pollinosis and can improve declined functions of the kidney and liver. The radiator A has a conspicuous effect on the improvement in the atopic dermatitis particularly when an amount thereof is increased to about 30 wt. %.

The powdered far-infrared radiator A can be held directly on a cloth-like holder such as cloth, paper or plastic film or indirectly on a member bonded to the holder, whereby the radiator A serves for care or first aid as a taping member as used in sports, poultice, or sticking or adhesive plaster. Thus, the powdered far-infrared radiator A can easily be held on the cloth-like holder such as cloth, paper, plastic film, etc. When the cloth-like holder is applied to or wound on a human body, the characteristic of radiating far-infrared rays can be utilized for care or first aid. In this case, when held on the cloth-like holder, the powdered far-infrared radiator A may be mixed with an adhesive agent to be applied to the cloth-like holder. Regarding cloth and paper, the radiator may be caused to permeate fiber or thread which is woven into the cloth, thereby to be held. The powdered far-infrared radiator A used preferably ranges 0.5 to 3 g per centare.

Furthermore, when mixed with an adhesive agent, the powdered far-infrared radiator used preferably ranges 3 to 5 weight percentage.

Figure 4:
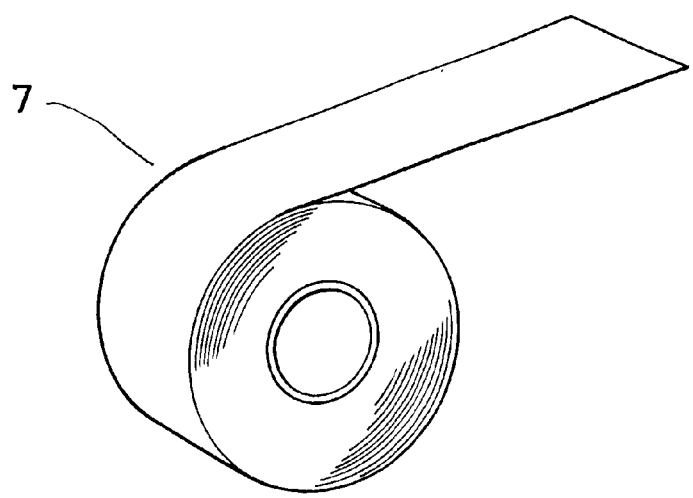
FIG. 4 illustrates a tape to which the powdered far-infrared radiator is applied.
Figure 5:
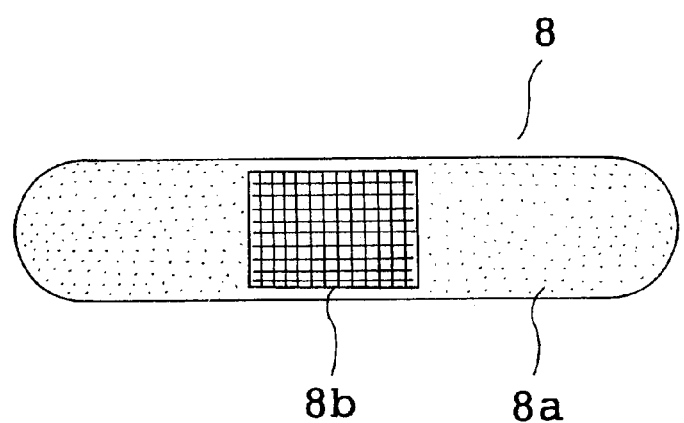
FIG. 5 illustrates a sticking plaster to which the powdered far-infrared radiator is applied.

More specifically, as shown in FIG. 4, the powdered far-infrared radiator A can be used as a taping member 7 as used in sports (called "kinesiotape") or the like by holding the radiator on a tape or bandage. Thus when the taping member 7 is wound on a wrist, ankle, calf, knee, waist or the like, improvements in the pain soothing and protection of an affected part can be achieved. Furthermore, as shown in FIG. 5, the powdered far-infrared radiator A can be used for a first-aide plaster 8 including an adhesive tape 8a holding a disinfect gauze 8b thereon. In this case, the radiator A may be held on the disinfect gauze 8b part or mixed with adhesive agent of the tape 8b. As a result, a wound can be sterilized and disinfected, whereupon the wound can be cured quickly.

Figure 6:
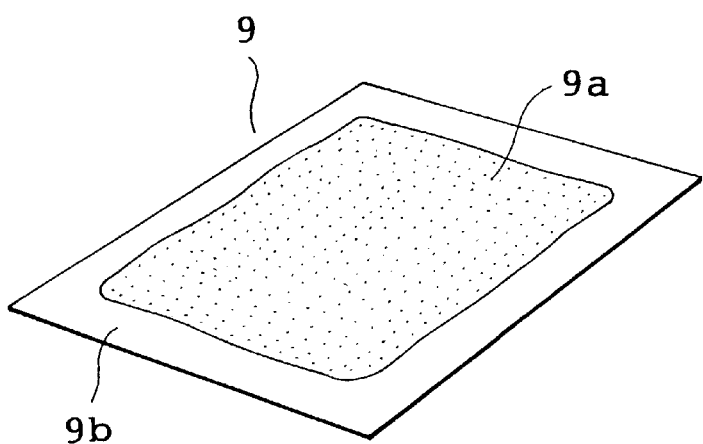
FIG. 6 illustrates a poultice to which the powdered far-infrared radiator is applied.

As shown in FIG. 6, a mixture of the radiator A and a salve 9a can be used as an antiphlogistic poultice 9 when applied to a cloth-like holder 9b. Consequently, an antiphlogistic effect of the poultice can be improved. Furthermore, the radiator A held on a cloth-like holder may be used as a packing member for beauty although not shown. Consequently, a good effect can be achieved for skin. When the radiator A held on the cloth-like holder is attached to eyes of a sufferer, the sufferer can be relieved from asthenopia.

Figure 7:
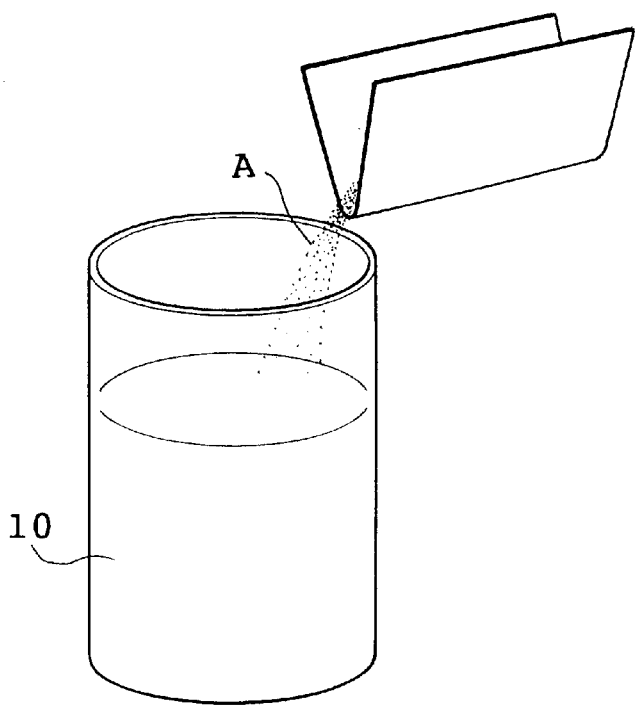
FIG. 7 illustrates a beverage to which the powdered far-infrared radiator is applied.

Furthermore, the powdered far-infrared radiator A may be mixed with a beverage or food so as to be used for promotion of one's health. More specifically, as shown in FIG. 7, one's health can be promoted when one just drinks a solution of the radiator A in water 10. The inventor confirmed that the powdered far-infrared radiator A was able to improve the functions of internal organs of a human body thereby to provide a desirable physical condition and promote one's health when orally taken into the human body. When the radiator A is used for eating and drinking purposes, the grain diameter thereof is preferably reduced to be at or below 0.8 $\mu$m. Additionally, cattle's health can be improved when the radiator A is mixed with stock feed.

Additionally, the powdered far-infrared radiator A can be used as a product facilitating blood circulation in a human body when held on personal ornaments such as underwear, socks, stockings, headband, caps, hats, etc. and bedding such as Japanese "futon" or thick bedquilt, bed sheets and mattress. In this case, the powdered far-infrared radiator A may be mixed with cotton wool of the Japanese "futon" as well as held on cloth. The radiator A can further be applied to a shoe insole, paper slippers, etc. by making use of a bactericidal action and an antibacterial action thereof. The radiator A can still further serve as a material for packaging perishable foods (paper bags and corrugated cardboard containers) and be mixed with a paint, whereupon a range of use of the radiator A can be increased. Corrosion can be limited when the radiator A is mixed with a paint, whereupon the radiator is effective for salt damage or injury. Particularly when the radiator A having a grain diameter not exceeding 0.2 $\mu$m is applied to a ship bottom paint, the ship bottom can be prevented from being barnacled by the action of reducing a surface salinity.

The foregoing description and drawings are merely illustrative of the principles of the present invention and are not to be construed in a limiting sense. Various changes and modifications will become apparent to those of ordinary skill in the art. All such changes and modifications are seen to fall within the scope of the invention as defined by the appended claims.

I claim:

1. A powdered far-infrared radiating material comprising a quartz schist comprising 80 to 90 wt. % $SiO_2$, 8 to 9 wt. % $Al_2O_3$ and 0.7 to 0.8 wt. % $Fe_2O_3$, the powder having a grain diameter not exceeding 6 $\mu$m and radiating far-infrared rays at or below 20° C., wherein the powder is prepared by heating at a temperature ranging from 200° C. to 400° C.

2. A topical cosmetic or medical cream or liquid comprising the powdered far-infrared radiating material according to claim 1.

3. A tape or bandage material holding the powdered far-infrared radiation material according to claim 1.

4. A beverage or food comprising the powdered far-infrared radiation material according to claim 1.

5. A method of making a powdered far-infrared radiating material comprising a quartz schist comprising 80 to 90 wt. % $SiO_2$, 8 to 9 wt. % $Al_2O_3$ and 0.7 to 0.8 wt. % $Fe_2O_3$, the powder having a grain diameter not exceeding 6 $\mu$m; and radiating far-infrared rays at or below 20° C., the method comprising:

grinding the quartz schist into a powder having a grain diameter not exceeding 6 $\mu$m; and heat-treating the powder at a temperature ranging from 200° C. to 400° C.

6. A stock feed for a domestic or farm animal comprising the powdered far-infrared radiating material according to claim 1.

7. A marine paint comprising the powdered far-infrared radiating material according to claim 1.

8. A personal ornament comprising the powdered far-infrared radiating material according to claim 1.

* * * * *